United States Patent
Seo et al.

(10) Patent No.: US 6,998,492 B2
(45) Date of Patent: Feb. 14, 2006

(54) ORGANOMETALLIC COMPLEX AND LIGHT-EMITTING ELEMENT CONTAINING THE SAME

(75) Inventors: Satoshi Seo, Kanagawa (JP); Atsushi Tokuda, Kanagawa (JP); Hideko Inoue, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 125 days.

(21) Appl. No.: 10/840,151

(22) Filed: May 6, 2004

(65) Prior Publication Data

US 2004/0230061 A1 Nov. 18, 2004

(30) Foreign Application Priority Data

May 16, 2003 (JP) ........................................ 2003-138862

(51) Int. Cl.
*C07F 15/00* (2006.01)
*H05B 33/14* (2006.01)

(52) U.S. Cl. .............................. 548/402; 546/4; 546/10; 313/503; 313/504; 313/506; 428/690; 428/917; 257/102

(58) Field of Classification Search ..................... 546/4, 546/10; 548/402; 428/690, 917; 313/503, 313/504, 506; 257/102
See application file for complete search history.

(56) References Cited

U.S. PATENT DOCUMENTS

| | | | | |
|---|---|---|---|---|
| 6,787,249 B2 * | 9/2004 | Seo | ........................... | 428/690 |
| 2003/0022019 A1 * | 1/2003 | Seo et al. | ................... | 428/690 |
| 2004/0241493 A1 * | 12/2004 | Inoue et al. | ................ | 428/690 |
| 2005/0001543 A1 * | 1/2005 | Nomura et al. | ............. | 313/504 |
| 2005/0048317 A1 * | 3/2005 | Seo et al. | .................... | 428/690 |

OTHER PUBLICATIONS

Tsutsui, T. et al, "High Quantum Efficiency in Organic Light–Emitting Devices with Iridium–Complex as a Triplet Emissive Center," Japanese Journal of Applied Physics, vol. 38, part 2, No. 12B, pp. L1502–L1504, Dec. 15, (1999).

Thompson, M.E. et al, "Phosphorescent Materials and Devices," 10th International Workshop on Inorganic and Organic Electroluminescence, pp. 35–37, (2000).

* cited by examiner

*Primary Examiner*—Porfirio Nazario-Gonzalez
(74) *Attorney, Agent, or Firm*—Cook, Alex, McFarron, Manzo, Cummings & Mehler, Ltd.

(57) ABSTRACT

Organometallic complexes represented by chemical formula 1 are synthesized. In chemical formula 1, $R^1$ to $R^5$, are individually a hydrogen atom, a halogen atom, a lower alkyl group, an alkoxy group, an acyl group, a nitro group, a cyano group, an amino group, a dialkylamino group, a diarylamino group, a vinyl group, an aryl group, or a heterocyclic group. Each pair of $R^1$ and $R^2$, $R^2$ and $R^3$, and $R^4$ and $R^5$ may be bonded each other to form aromatic rings. Y is a heterocyclic group containing nitrogen atoms as hetero atoms. M is atoms of group 9 in the periodic table or atoms of group 10 in the periodic table. When the M is atoms of group 9 in the periodic table, n=2. When the M is atoms of group 10 in the periodic table, n=1. L is a monoanionic bidentate chelate ligand having a beta diketone structure, a monoanionic bidentate chelate ligand having a carboxyl group, or a monoanionic bidentate chelate ligand having a phenol hydroxyl group.

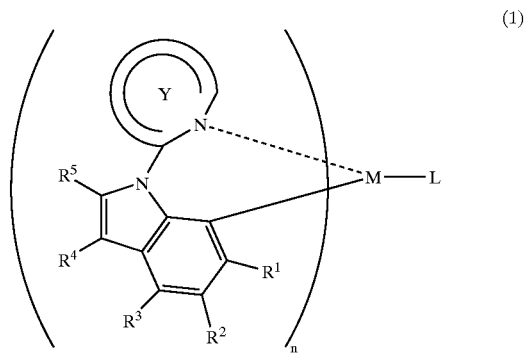

(1)

40 Claims, 5 Drawing Sheets

ORGANOMETALLIC COMPLEX AND LIGHT-EMITTING ELEMENT CONTAINING THE SAME

BACKGROUND OF THE INVENTION

1. Field of the Invention

The present invention relates to an organometallic complex which can generate light emission from a triplet excited state to emit phosphorescence, and a light-emitting element containing the organometallic complex.

2. Related Art

Organic compounds (organic molecules) undergo a transition to an upper electronic state (excited state) when absorbing light. By way of the excited state, various reactions (photochemical reactions) may be occurred, or light emission (luminescence) may be generated. There are various applications of the organic compounds.

As an example of photochemical reactions, production and reaction of singlet oxygen can be nominated. Since the ground state of oxygen molecules is a triplet state, singlet state oxygen (singlet oxygen) is not produced by direct photoexcitation. However, in the presence of another triplet excited molecules, singlet oxygen is produced. In this instance, compounds capable of forming the foregoing triplet exited molecules are referred to as photosensitizer, and utilized as, for example, photobleaching agent or antimicrobial activity compounds.

As stated above, in order to produce singlet oxygen, photosensitizer which can form triplet excited molecules by photoexcitation is required. However, since the ground state of general organic compounds is a singlet state, the photo-excitation to a triplet excited state is a forbidden transition, that is, the probability of generating triplet excited molecules is very small (generally, singlet excited molecules are generated). Therefore, as the photosensitizer, compounds that are susceptible to give rise to intersystem crossing from a singlet excited state to a triplet excited state (or compounds that allow the forbidden transition that photoexcitation to a triplet excitation state) are required. In other words, such compounds are beneficial in using as photosensitizer. Further, such compounds may emit phosphorescence.

In recent years, materials emitting phosphorescence have attracted attention as light-emitting substances used for a light-emitting element such as an electroluminescent (EL) element.

Phosphorescence is the light emission occurs from a transition between electronic states of different multiplicities, that is, the light emission occurs from the triplet excited state back to the singlet ground state. Further, fluorescence is the light emission that occurs from the singlet excited state back to the singlet ground state.

The compounds that can emit phosphorescence, that is, the compounds that can generate light emission from the triplet excited state (hereinafter, phosphorescent compounds) have high internal quantum efficiency of from 75 to 100% in theory. The value is approximately three to four times as large as that of compounds that emit fluorescence. Therefore, a high efficient light-emitting element can be manufactured by phosphorescent compounds.

However, many of materials that have been conventionally used as light-emitting substances emit fluorescence. Phosphorescent compounds are very few in number. Therefore, many chemists have developed the phosphorescent compounds. (For example, refers to Tetsuo Tsutsui et al. "Japanese Journal of Applied Physics", vol. 38, L1502–L1504 (1999), and M. A. Baldo et al. "Nature (London)", vol. 403, 750–753 (2000).)

In the above both references, an organometallic compound containing iridium as a central metals is disclosed. The organometallic compound is a type of organometallic complexes referred to as an orthometallic compound.

The structures of ligands of iridium complexes disclosed in the above both references are comparatively simple. The iridium complexes can give green emission with good color purity. In order to control the emission color, it is necessary to change the structure of the ligands. For example, M. Thompson et al. disclosed that they achieved some emission colors by synthesizing various ligands and iridium complexes containing the foregoing various ligands in "10$^{th}$ International Workshop on Inorganic and Organic Electroluminescence (EL '00)", 35–38.

However, almost the foregoing ligands of iridium complexes are confined to those that can form five-membered rings with central metals. The present situation is that appropriate emission color is explored from the foregoing confined ligands. That is, the fact is problematic that applicable kinds of ligands are very few in number.

In addition, many of the foregoing ligands have difficulty synthesizing, and so the number of processes for synthesizing is large. As a result, the cost of materials is increased. In view of the cost, the yield of organometallic complexes is one of the important factors.

Further, problems have been arisen in case of using organometallic complexes for an electronic device such as a light-emitting element since organometallic complexes are susceptible to be decomposed and have poor heat resistance properties.

Accordingly, the development of organometallic complexes is required which can synthesize ligands easily, which can be synthesized with good yields, and which have excellent heat resistance properties.

SUMMARY OF THE INVENTION

In view of the foregoing, it is an object of the present invention to provide organometallic complexes which can synthesize ligands easily, which can be synthesized with good yields, which have excellent heat resistance properties, and which can generate light emission from the triplet excited states; and a light-emitting element containing the organometallic complexes.

The invention provides the organometallic complex represented by general formula 1.

(1)

wherein $R^1$ to $R^5$, each of which may be the same or different, are individually a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic group which may have a substituent. Each pair of $R^1$ and $R^2$, $R^2$ and $R^3$, and $R^4$ and $R^5$ may be bonded each other to form aromatic rings. Y is a heterocyclic group containing a nitrogen atom as a hetero atom. M is an atom of group 9 in the periodic table or an atom of group 10 in the periodic table. When the M is the atom of group 9 in the periodic table, n=2. When the M is the atom of group 10 in the periodic table, n=1. L is a monoanionic bidentate chelate ligand having a beta diketone structure, a monoanionic bidentate chelate ligand having a carboxyl group, or a monoanionic bidentate chelate ligand having a phenol hydroxyl group.

The invention provides the organometallic complex represented by general formula 2.

(2)

wherein $R^{10}$ is a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic group which may have a substituent. Y is a heterocyclic group containing a nitrogen atom as a hetero atom. M is an atom of group 9 in the periodic table or an atom of group 10 in the periodic table. When the M is the atom of group 9 in the periodic table, n=2. When the M is the atom of group 10 in the periodic table, n=1. L is a monoanionic bidentate chelate ligand having a beta diketone structure, a monoanionic bidentate chelate ligand having a carboxyl group, or a monoanionic bidentate chelate ligand having a phenol hydroxyl group.

In the organometallic complex represented by general formula 1, $R^4$ and $R^5$ form aromatic rings to form the carbazole ligands represented by general formula 2. As a result, a process for synthesizing ligands, which is one of the processes for synthesizing the organometallic complexes according to the invention, can be facilitated. Moreover, a process for forming complexes can be facilitated, consequently, the yields are improved.

In the organometallic complex represented by the foregoing general formula 1 or 2, the Y is preferably a heterocyclic group containing a five-membered ring or a six-membered ring, which has conformation hard to prevent coordination to metals. More preferably, the organometallic complex represented by the following general formula 3 or 4. As the heterocyclic group containing a five-membered ring or a six-membered ring, a 2-pyridyl group, a 2-oxazolyl group, a 2-thiazolyl group, and the like can be nominated. Therefore, a process for forming a complex, which is one of the processes for synthesizing the organometallic complex according to the invention, can be facilitated. Consequently, the yields are improved.

(3)

wherein $R^1$ to $R^9$, each of which may be the same or different, are individually a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic group which may have a substituent. Each pair of $R^1$ and $R^2$, $R^2$ and $R^3$, $R^4$ and $R^5$, $R^6$ and $R^7$, $R^7$ and $R^8$, and $R^8$ and $R^9$ may be bonded each other to form aromatic rings. M is an atom of group 9 in the periodic table or an atom of group 10 in the periodic table. When the M is the atom of group 9 in the periodic table, n=2. When the M is the atom of group 10 in the periodic table, n=1. L is a monoanionic bidentate chelate ligand having a beta diketone structure, a monoanionic bidentate chelate ligand having a carboxyl group, or a monoanionic bidentate chelate ligand having a phenol hydroxyl group.

(4)

wherein $R^6$ to $R^{10}$, each of which may be the same or different, are individually a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic group which may have a substituent. Each pair of $R^6$ and $R^7$, $R^7$ and $R^8$, and $R^8$ and $R^9$ may be bonded each other to form aromatic rings. M is an atom of group 9 in the periodic table or an atom of group 10 in the periodic table. When the M is the atom of group 9 in the periodic table, n=2. When the M is the atom of group 10 in the periodic table, n=1. L is a monoanionic bidentate chelate ligand having a beta diketone structure, a monoanionic bidentate chelate ligand having a carboxyl group, or a monoanionic bidentate chelate ligand having a phenol hydroxyl group.

In the organometallic complexes represented by the foregoing general formula 1, 2, 3, or 4, as a lower alkyl group, a methyl group, an ethyl group, an n-propyl group, an isopropyl group, an n-butyl group, a sec-butyl group, a tert-butyl group, a hexyl group, and the like are nominated, and those of which have preferably carbon atoms of from 1 to 6. An alkyl halide group such as a trifluoromethyl group, or a cycloalkyl group such as a cyclohexyl group may also be used. As an alkoxy group, a methoxy group, an ethoxy group, an n-propoxy group, an isopropoxy group, an n-butoxy group, a sec-butoxy group, a tert-butoxy group, a hexoxy group, and the like are nominated. As an acyl group, an acetyl group is nominated. As a dialkylamino group, a dimethylamino group, a diethylamino group, and the like are nominated, and those of which have preferably carbon atoms of from 1 to 4. As a diarylamino group, a diphenylamino group, a bis($\alpha$-naphtyl)amino group, and the like are nominated. Alternatively, a substituted arylamino group such as bis(m-tolyl)amino group may be used. As a vinyl group, a vinyl group having a substituent such as diphenylvinyl group may be used. As an aryl group, besides a nonsubstituted aryl group such as a phenyl group or a naphthyl group, a substituted aryl group such as an o-tolyl group, an m-tolyl group, a p-tolyl group, a xylyl group, a methoxyphenyl group, an ethoxyphenyl group, a fluorophenyl group may be used. In addition, as a heterocyclic group, a pyridyl group, a furyl group, a thienyl group, and the like are nominated. They may have additionally a substituent such as a methyl group.

In the organometallic complex represented by the foregoing general formula 1, 2, 3, or 4, the central metal M is an iridium atom or a platinum atom. By using heavy atoms such as the iridium atoms or the platinum atoms as the central metal, phosphorescence can be further efficiently obtained.

In the organometallic complex represented by the foregoing general formula 1, 2, 3, or 4, the ligand L is preferably a monoanionic bidentate chelate ligand having a beta diketone structure, a monoanionic bidentate chelate ligand having a carboxyl group, or a monoanionic bidentate chelate ligand having a phenol hydroxyl group. More preferably, the L is any one of monoanionic bidentate chelate ligands represented by the following structural formulae 5 to 11. These monoanionic bidentate chelate ligands have high capability of coordination and are inexpensive.

The above mentioned organometallic complex forms a six-membered ring with a central metal. Further, the organometallic complex according to the invention can emit light from the triplet excited state. That is, the organometallic complexes can emit phosphorescence.

Another aspect of the invention is a light-emitting element containing the organometallic complex represented by the foregoing general formula 1, 2, 3, or 4. A light-emitting element with high emission efficiency can be manufactured by the organometallic complex according to the invention as light-emitting substances.

Specifically, the light-emitting element according to the invention has a layer formed by the organometallic complex represented by the foregoing general formula 1, 2, 3, or 4 between a pair of electrodes. In this way, the organometallic complex according to the invention can be used as a light-emitting layer.

Further, the light-emitting element according to the invention has a layer formed by the organometallic complexes represented by the foregoing general formula 1, 2, 3, or 4. In this way, the organometallic complexes according to the invention can be used as guest materials for a light-emitting layer.

These and other objects, features and advantages of the present invention will become more apparent upon reading of the following detailed description along with the accompanied drawings.

DESCRIPTION OF THE INVENTION

[Embodiment 1]

Hereinafter, a method for synthesizing an organometallic complex according to the invention will be explained as one mode of the present invention.

A ligand represented by general formula 12 is synthesized by synthesis scheme a-1.

In general formula 12 and synthesis scheme a-1, $R^1$ to $R^5$, each of which may be the same or different, are individually a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or heterocyclic group which may have a substituent. Each pair of $R^1$ and $R^2$, $R^2$ and $R^3$, and $R^4$ and $R^5$ may be bonded each other to form an aromatic ring.

As a lower alkyl group, a methyl group, an ethyl group, an n-propyl group, an isopropyl group, an n-butyl group, a sec-butyl group, a tert-butyl group, a hexyl group, and the like are nominated, and those of which have preferably carbon atoms of from 1 to 6. An alkyl halide group such as a trifluoromethyl group, or a cycloalkyl group such as a cyclohexyl group may also be used. As an alkoxy group, a methoxy group, an ethoxy group, an n-propoxy group, an isopropoxy group, an n-butoxy group, a sec-butoxy group, a tert-butoxy group, a hexoxy group, and the like are nominated, and those of which have preferably carbon atoms of from 1 to 6. As an acyl group, an acetyl group is nominated. As a dialkylamino group, a dimethylamino group, a diethylamino group, and the like are nominated, and those of which have preferably carbon atoms of from 1 to 4. As a diarylamino group, a diphenylamino group, a bis(α-naphtyl)amino group, and the like are nominated. Alternatively, a substituted arylamino group such as bis(m-tolyl)amino group may be used. As a vinyl group, a vinyl group having a substituent such as diphenylvinyl group may be used. As an aryl group, in addition to a nonsubstituted aryl group such as a phenyl group or a naphthyl group, a substituted aryl group such as an o-tolyl group, an m-tolyl group, a p-tolyl group, a xylyl group, a methoxyphenyl group, an ethoxyphenyl group, a fluorophenyl group may be used. In addition, as a heterocyclic group, a pyridyl group, a furyl group, a thienyl group, and the like are nominated. They may have additionally a substituent such as a methyl group.

In general formula 12 and synthesis scheme a-1, as the heterocyclic group Y, a five-membered ring or a six-membered ring is preferably used in consideration for conformation which can coordinate without preventing the coordination to the central metal M. Consequently, synthesis becomes easy to carry out with good yields. Specifically, a 2-pyridyl group, a 4-pyrimidyl group, a 2-oxazolyl group, a 2-thiazolyl group, or the like can be used. The 2-pyridyl group is, but not exclusively, most preferably used among others. For example, a polycyclic group such as a 2-benzooxazolyl group can be used.

The organometallic complex according to the invention represented by general formula 13 are synthesized using a ligand represented by general formula 12 by cyclometallization reactions represented by synthesis schemes a-1 and a-3.

(13)

-continued (a-2)

(a-3)

In general formula 13, and synthesis schemes a-2 and a-3, Y is the one illustrated in general formula 12 and L is a monoanionic bidentate chelate ligand having a beta diketone structure, a monoanionic bidentate chelate ligand having a carboxyl group, or a monoanionic bidentate chelate ligand having a phenol hydroxyl group. Specifically, acetylacetone, dimethyl malonate, picolinic acid, proline, salicylideneamine, salicylaldehyde, 8-quinolinol, or the like can be used.

As represented by synthesis scheme a-2, hydrate of iridium chloride as a central metal material and a ligand represented by general formula 12 are mixed and refluxed under a nitrogen atmosphere, and a chorine-bridged dimer complex is synthesized. Then, as represented by synthesis scheme a-3, the obtained dinuclear complexes and the bidentate chelate ligand are mixed and refluxed under a nitrogen atmosphere to split the chlorine bridging by the bidentate chelate ligand L. Consequently, the organometallic complexes represented by general formula 13 according to the invention are obtained.

In the ligand represented by general formula 12, substances except hydrogen atoms, for example, a lower alkyl group such as a methyl group, or a substituent such as a vinyl group can be used for $R^5$, accordingly, central metals (iridium atoms (Ir) in this embodiment) become easy to bond to the 7-position of indole. That is, the reaction site becomes easy to be fixed to in one place, and the yield is improved.

Futher, in the ligand represented by general formula 12, $R^4$ and $R^5$ form aromatic rings, consequently, a carbazole ligand as represented by general formula 14 is produced. In this case, central metals (iridium atoms in this embodiment) become easy to bond to the 1 or 8-position of carbazole. Since the 1 or 8-position of carbazole are equivalent to each other, organometallic complexes having the same structure can be synthesized by the bond of the carbazole and the central metals at any reaction site. Therefore, it can lead to the improvement of yields.

(14)

In the formula, $R^{10}$ is a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or heterocyclic group which may have a substituent. Y is a heterocyclic group containing a nitrogen atom as a hetero atom.

Accordingly, the organometallic complex according to the invention can be obtained by the above mentioned synthesis method. However, the synthesis method for the organometallic complexes according to the invention is not limited thereto.

As specific examples of ligand represented by general formulae 12 and 14, 1-(2-pyridyl)indole, 1-(2-pyridyl)-2-methylindole, 1-(2-pyridyl)-5-methoxyindole, 1-(2-pyridyl)-5-dimethylaminoindole, 1-(2-pyridyl)-5-diphenylaminoindole, 1-(2-pyridyl)-5-diphenylvinylindole, 1-(2-oxazolyl)indole, 1-(2-thiazolyl)indole, 9-(2-pyridyl)-carbazole, 9-(2-pyridyl)-3,6-dimethylcarbazole, 9-(2-pyridyl)-3,6-dimethoxycarbazole, 9-(2-pyridyl)-3,6-bis(diphenylamino)carbazole, 9-(2-pyridyl)-3,6-bis(diphenylvinyl)carbazole, 9-(2-oxazolyl)carbazole, 9-(2-thiazolyl)carbazole, and the like can be nominated, but not exclusively.

The following structural formulae 15 to 22 are specific examples of the organometallic complexes according to the invention obtained by the above synthesis method. However, the organometallic complexes according to the invention are not limited thereto. In the following specific examples, an example that uses platinum (Pt) atoms instead of iridium (Ir) atoms is also described.

(15)

(16)

(17)

(18)

(19)

(20)

(21)

(22)

Each of the above mentioned organometallic complexes according to the invention has the structure that forms a six-membered ring with central metals, and can emit light occurred from the triplet excited state. That is, the organometallic complexes emit phosphorescence. The organometallic complexes according to the invention can be synthesized with good yields, and so manufactured at low cost. Further, the organometallic complexes according to the invention can be applied to a light-emitting element as phosphorescent materials. In addition, the organometallic complexes can be used as sensitizer as described in M. A. Baldo et al. "Nature (London)", vol. 403, 750–753 (2000). Besides, the organometallic complexes according to the invention are susceptible to give rise to intersystem crossing, hence, the organometallic complexes according to the invention can be used as photobleaching agent or antibacterial compounds as photosensitizer.

[Embodiment 2]

In this embodiment, as one aspect of the present invention, a light-emitting element containing the organometallic complexes according to the present invention will be explained with reference to FIG. 1.

Figure 1:
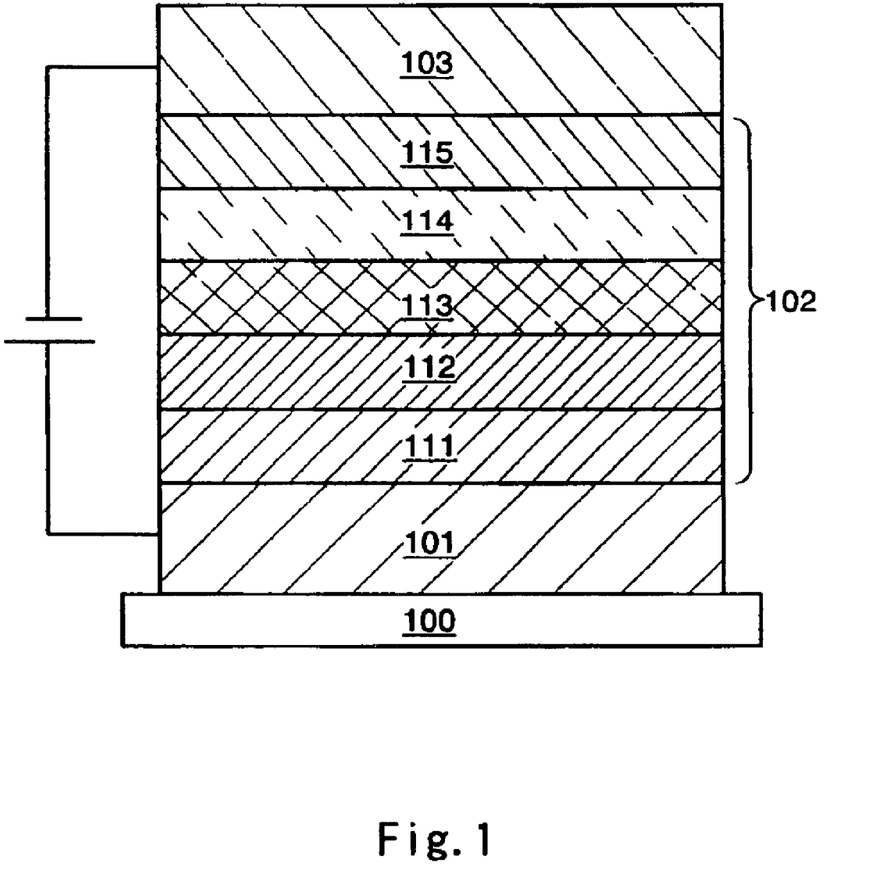
FIG. 1 is an explanatory view of one mode of a light-emitting element according to the present invention.

As shown in FIG. 1, a first electrode 101 is formed over a substrate 100, and a layer containing light-emitting substances is formed over the first electrode 101, then, a second electrode 103 is formed thereover.

As materials for the substrate 100, anything can be used, which is used for the conventional light-emitting element, for example, glass, quartz, transparent plastics, or the like can be used.

In this embodiment, the first electrode 101 serves as an anode, and the second electrode 103 serves as a cathode.

Therefore, the first electrode 101 is formed by anode materials. As materials for the anode, metals having large work functions (at least 4.0 eV), alloys, compounds having electrical conduction properties, and mixture of these materials can be preferably used as anode materials. As specific examples of the anode materials, aurum (Au), platinum (Pt), nickel (Ni), tungsten (W), chrome (Cr), molybdenum (Mo), ferrum (Fe), cobalt (Co), copper (Cu), palladium (Pd), nitride of metal materials (for example, TiN), or the like can be used, besides ITO (indium tin oxide) or IZO (indium zinc oxide) composed of indium oxide mixed with zinc oxide (ZnO) of from 2 to 20%.

As cathode materials for forming the second electrode 103, metals having small work functions (at most 3.8 eV), alloys, compounds having electrical conduction properties, mixture of these materials, or the like is preferably used as cathode materials. As specific examples of the cathode materials, an element in the first or second periodic row, that is, an alkali metal such as Li, Cs, or the like; alkali earth metal such as Mg, Ca, Sr, or the like; or alloys of these elements (Mg:Ag, Al:Li) can be used. By stacking a layer promoting injection of electrons between the second electrode 103 and a light-emitting layer, various conductive materials such as Al, Ag, ITO, or the like can be used regardless of the work functions for the second electrode 103.

As the layer promoting injection of electrons, compounds of alkali metals or alkali earth metals such as lithium fluoride (LiF), cesium fluoride (CsF), calcium fluoride ($CaF_2$), or the like can be used. Besides, materials having electron transportation properties containing alkali metals or alkali earth metals, for example, Alq containing magnesium (Mg), or the like can be used.

The above anode and cathode materials are deposited by vapor deposition or sputtering to form a thin film as the first electrode 101 and the second electrode 103, respectively.

In a light-emitting element according to the invention, light generated by recombination of carries within a layer containing light-emitting substances emits from either the first electrode 101 or the second electrode 103, or both of the electrodes. When light emits from the first electrode 101, the first electrode 101 is formed by materials having light transmission properties. When light emits from the second electrode 103, the second electrode 103 is formed by materials having light transmission properties.

The light-emitting layer 102 is formed by stacking a plurality of layers. In this embodiment, the light-emitting layer 102 is formed by stacking a hole injecting layer 111, a hole transporting layer 112, a light-emitting layer 113, a hole blocking layer 114, and an electron transporting layer 115.

In this instance, as hole injection materials for forming the hole injecting layer 111, phthalocyanine-based compounds can be efficiently used. For example, phthalocyanine (hereinafter, $H_2$-Pc), copper phthalocyanine (hereinafter, Cu-Pc), or the like can be used.

As hole transportation materials for forming the hole transporting layer 112, aromatic amine (that is, the one having a benzene ring-nitrogen bond) based compounds are preferably used. For example, besides 4,4'-bis[N-(3-methylphenyl)-N-phenyl-amino]-biphenyl (hereinafter, TPD), derivatives thereof such as 4,4'-bis[N-(1-naphthyl)-N-phenyl-amino]-biphenyl (hereafter, a-NPD) is widely used. Also used are star burst aromatic amine compounds, including 4,4',4"-tris(N,N-diphenyl-amino)-triphenyl amine (hereafter, TDATA), and 4,4',4"-tris[N-(3-methylphenyl)-N-phenyl-amino]-triphenyl amine (hereafter, MTDATA).

The light-emitting layer 113 contains the organometallic complex represented by general formula 1, 2, 3, or 4. In this embodiment, the organometallic complex represented by general formula 1, 2, 3, or 4 is used as a guest material. In this case, the light-emitting layer may be formed by co-evaporating the organometallic complex represented by general formula 1, 2, 3, or 4 and a host material. A known materials can be used as the host material, for example, 4,4'-N,N'-di carbazolyl-biphenyl (abbreviated CBP), 2,2',2"-(1,3,5-benzenetri-yl)tris[1-phenyl-1H-benzimidazole] (abbreviated TPBI), or the like can be used.

As mentioned the above, the layer comprising the organometallic complex may be used as the light-emitting layer 113, but a layer consisting of the organometallic complex may be used as the light-emitting layer 113.

As hole blocking material for forming the hole blocking layer 114, bis(2-methyl-8-quinolinolate)-4-phenylphenolato-aluminum (abbreviated BAlq); 1,3-bis[5-(p-tert-butylphenyl)-1,3,4-oxadiazole-2-yl]benzene (abbreviated OXD-7); triazole derivatives such as 3-(4-tert-butylphenyl)-4-phenyl-5-(4-biphenylyl)-1,2,4-triazole (abbreviated TAZ); 3-(4-tert-butylphenyl)-4-(4-ethylphenyl)-5-(4-biphenylyl)-1,2,4-triazole (abbreviated p-EtTAZ); bathophenanthroline (abbreviated BPhen); and bathocuproin (abbreviated BCP) can be used.

As electron transportation material for forming the electron transporting layer 115, metal complexes having a quinoline skeleton or a benzoquinoline skeleton such as tris(8-quinolinolate) aluminum (abbreviated $Alq_3$), tris(5-methyl-8-quinolinolate) aluminum (abbreviated $Almq_3$), bis (10-hydroxybenzo[h]-quinolinato) beryllium (abbreviated $BeBq_2$), or the above mentioned BAlq is preferably used. Alternatively, a metal complex having oxazole based or thiazole based ligand such as bis [2-(2-hydroxyphenyl)-benzooxazolate] zinc (abbreviated $Zn(BOX)_2$), or bis [2-(2-hydroxyphenyl)-benzothiazolate] zinc (abbreviated $Zn(BTZ)_2$) can be used. Besides, 2-(4-biphenyl)-5-(4-tert-butylphenyl)-1,3,4-oxadiazole (abbreviated PBD); 1,3-bis [5-(p-tert-butylphenyl)-1,3,4-oxadiazole-2-yl]benzene (abbreviated OXD-7); 3-(4-tert-butylphenyl)-4-phenyl-5-(4-biphenylyl)-1,2,4-triazole (abbreviated TAZ) and 3-(4-tert-butylphenyl)-4-(4-ethylphenyl)-5-(4-biphenylyl)-1,2,4-triazole (abbreviated p-EtTAZ); bathophenanthroline (abbreviated BPhen), bathocuproin (abbreviated BCP), or the like can be used in addition to metal complexes.

Accordingly, a light-emitting element composed of the hole injecting layer 111, the hole transporting layer 112, the hole blocking layer 114, and the electron transporting layer 115, each of which is formed by a low molecular weight material; and the light-emitting layer 113 containing the organometallic complex according to the invention can be manufactured. In addition, as host materials for the hole injecting layer 111, the hole transporting layer 112, the hole blocking layer 114, the electron transporting layer 115, and the light-emitting layer 113, an intermolecular weight material such as dendrimer or oligomer, or a high molecular weight material can be used in addition to the low molecular weight material. With respect to a method for film formation, another method such as ink jetting can be used in addition to vapor deposition.

Figure 2:
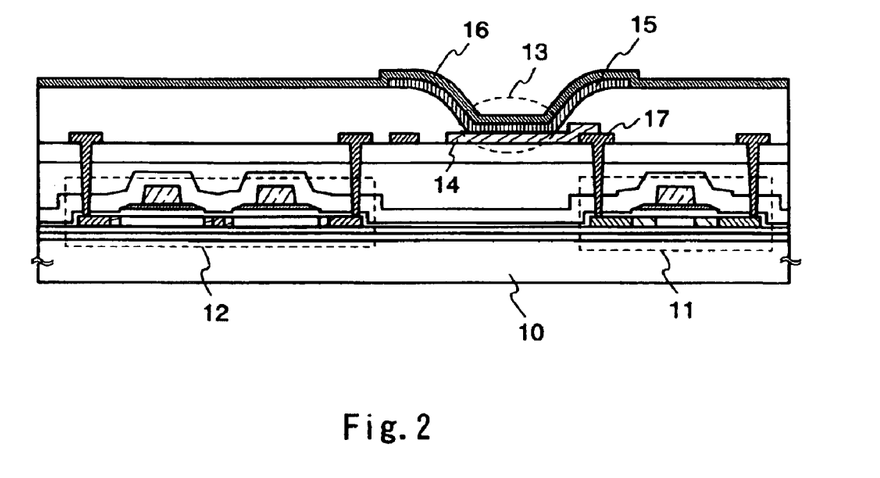
FIG. 2 is an explanatory view of one mode of a light-emitting element according to the invention.

In this embodiment, a light-emitting element is formed over the substrate 100 formed by glass, quartz, transparent plastics, or the like, but not exclusively. For example, the light-emitting element can be formed over a thin film transistor (TFT) array substrate as shown in FIG. 2. In FIG. 2, reference numeral 10 denotes a substrate; 11 and 12 encircled by a dotted line, TFTs; 14, a first electrode; 15, a layer containing light-emitting substances; 16, a second electrode; and 17, wiring. The region where the first electrode, the layer containing light-emitting substances 15, and the second electrode 16 are stacked serves as a light-emitting element 13. Accordingly, an active matrix light-emitting device which controls the drive of a light-emitting element by TFTs can be manufactured. In addition, the structure of TFTs are not especially limited, either a top gate type or a bottom gate type can be employed.

The configuration of the layer containing light-emitting substances 102 is not limited to the above. The layer containing light-emitting substances 102 can be formed to have a lamination configuration which is different from that mentioned above. For example, in addition to a light-emitting layer, an electron injecting layer, an electron transporting layer, a hole blocking layer, a hole transporting layer, a hole injecting layer, and the like are stacked freely to form the lamination configuration: a hole injecting layer/a light-emitting layer/an electron transporting layer, a hole injecting layer/a hole transporting layer/a light-emitting layer/an electron transporting layer, a hole injecting layer/a hole transporting layer/a light-emitting layer/an electron transporting layer/an electron injecting layer, a hole injecting layer/a hole transporting layer/a light-emitting layer/a hole blocking layer/an electron transporting layer, a hole injecting layer/a hole transporting layer/a light-emitting layer/a hole blocking layer/an electron transporting layer/an electron injecting layer, or the like.

The organometallic complex according to the invention can generate light emission from the triplet excited state to emit phosphorescence. Therefore, by practicing the organometallic complex according to the invention, a light-emitting element which can emit light with high light emission efficiency. Accordingly, the power consumption of a light-emitting device installed with the light-emitting element according to the invention can be reduced.

EXAMPLES

Synthesis examples of organometallic complexes according to the present invention will be described hereinafter, but not limited to those described hereinafter.

Synthesis Example 1

A method for synthesizing the organometallic complex (abbreviated $Ir(pcz)_2(pic)$) represented by structural formula 7 according to the invention will be explained in this synthesis example 1.

[Step 1: Synthesis of Ligand (Hpcz)]

In 40 ml of o-dichlorobenzene as solvent, 3.94 g of carbazole, 7.26 g of 2-iondopyridine, 13.10 g of potassium carbonate, 3 g of copper powder, and 0.62 g of 18-crown-6-ether were mixed and refluxed under a nitrogen atmosphere for 10 hours. Thereafter, copper and inorganic salts were removed, and the mixture was purified by column chromatography. Consequently, ligand Hpcz (9-(2-pyridyl) carbazole) was obtained (opal powder, the yield: 93%). The following is the synthesis scheme (b-1).

(b-1)

Further, IR spectrum of the obtained product showed the result which suggests that N—H stretching vibration (3845 $cm^{-1}$) derived from carbazole was disappeared and the reaction was progressed.

[Step: 2 Synthesis of Dinuclear Complex ([Ir(pcz)$_2$CL]$_2$)

In mixture of 30 ml of 2-ethoxyethanol and 10 ml of water, 1.55 g of Hpcz obtained from the above synthesis (Step 1) and 0.76 g of iridium chloride (IrCL$_3$.HCL.H$_2$O) were mixed and refluxed under a nitrogen atmosphere for 14 hours. Consequently, the dinuclear complex ([Ir(pcz)$_2$CL]$_2$ was obtained (yellow powder, the yield of 91%). The following is the synthesis scheme (b-2).

(b-2)

[Step 3: Synthesis of Organometallic Complex [Ir(pcz)$_2$(pic)]]

Further, in 30 ml of 2-ethoxyethanol, 0.66 g of [Ir(pcz)$_2$CL]$_2$ obtained from the above synthesis (Step 2), 0.17 g of picolinic acid (Hpic), 0.48 g of sodium carbonate were mixed and refluxed under a nitrogen atmosphere for 26 hours. A phosphorescent compound [Ir(pcz)$_2$(pic)] according to the invention (yellow powder, the yield of 87%) was obtained by the recrystallization of the obtained yellow powder from ethanol solvent. The following is the synthesis scheme (b-3). The mass-analysis of the obtained yellow powder with ESI-MS showed the result as follows: m/z= 802. The H$^1$-NMR (nuclear magnetic resonance) spectrum of the yellow powder showed the result as the following. Consequently, the 2-pyridylcarbazole complex according to the invention was obtained.

$^1$H-NMR (300 MHz, DMSO-d6) d ppm: 8.18 (m, 5H), 7.91 (m, 6H), 7.78 (d, 1H), 7.65 (m, 2H), 7.50 (m, 6H), 6.92 (t, 1H), 6.18 (m, 2H), 6.70 (t, 1H), 6.40 (d, 1H) 5.75 (d, 1H).

(b-3)

The decomposition temperature $T_d$ of the organometallic complex obtained according to the invention was measured with TG-DTA (Themo Gravimetry/Differential Thermal Analysis (Seiko Instruments Inc., TG/DTA 320)) and the result was as follows: Td=381° C. Accordingly, the organometallic complexes were excellent in heat resistance properties, yields, and cost.

Figure 3:
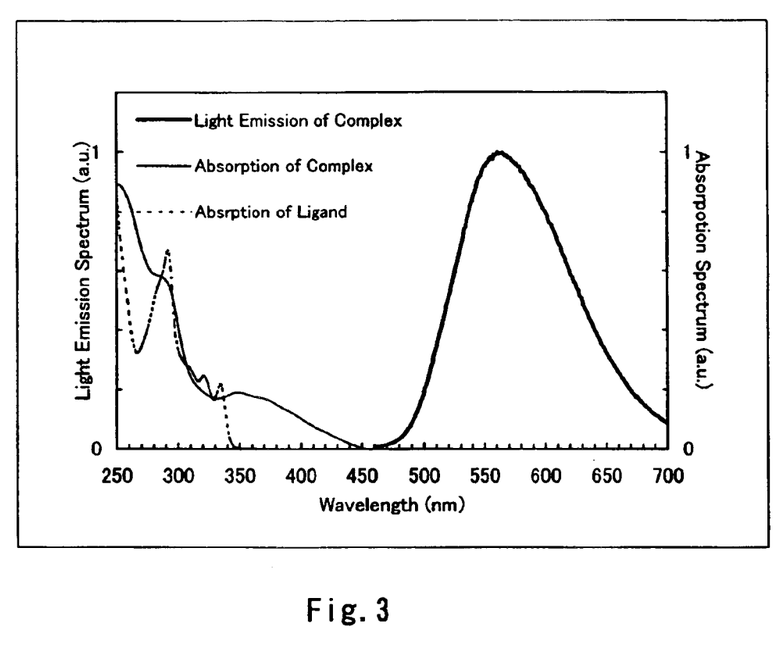
FIG. 3 is a view showing absorption and light emission spectra of organometallic complexes according to the invention.

FIG. 3 shows an absorption spectrum and light emission spectrum (PL) of dichloromethane of Ir(pcz)$_2$(pic). FIG. 3 shows also an absorption spectrum of a ligand. Ligand Hpcz had absorption peaks at 292 nm, 321 nm, and 334 nm. On the other hand, the organometallic complexes Ir(pcz)$_2$(pic) according to the invention has absorption peaks at four points of 286 nm, 349 nm, 370 nm, and 421 nm. Further, the emission spectrum of the yellow light emission showed a peak at 566 nm. The absorption spectrum of complexes shown in FIG. 3 had a broad absorption band overlapping with a visible light region. It can be considered that the formation of the triplet MLCT (metal to ligand charge transfer) state took place and that Ir(pcz)$_2$(pic) was the material susceptible to give rise to intersystem crossing.

[Comparative Example 1]

The conventional iridium complex (abbreviated Ir(tpy)$_2$(acac)) was synthesized. Then, the decomposition temperature $T_d$ thereof was measured with TG-DTA and the result was as follows: $T_d$=298° C.

(23)

Since the $T_d$ of the organometallic complex Ir(pcz)$_2$(Pic) according to the invention explained in Synthesis example 1 was 381° C., $T_d$ of the conventional iridium complex Ir(tpy)$_2$ (acac) was 80° C. lower than that of the organometallic complex. Therefore, the organometallic complex according to the invention are superior in heat resistance.

Example 1

Figure 4A:
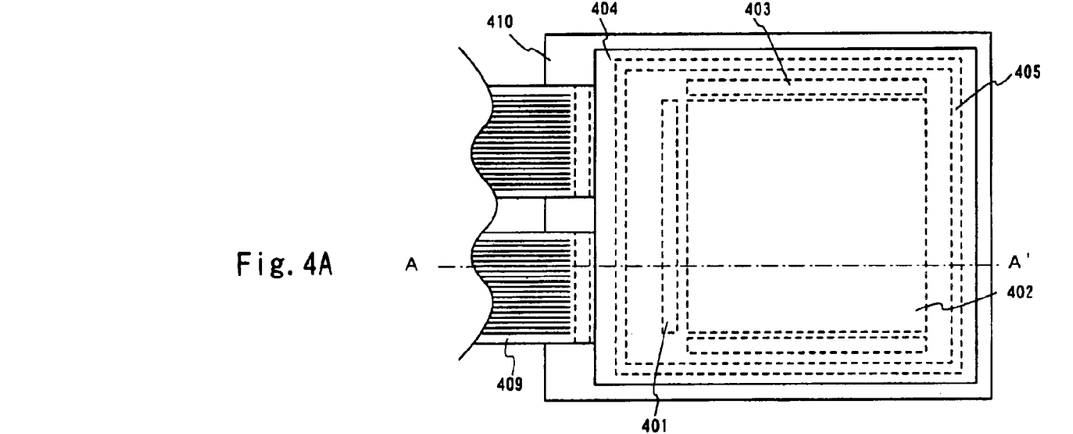
FIGS. 4A and 4B are explanatory views of a light-emitting device applied with the invention.
Figure 4B:
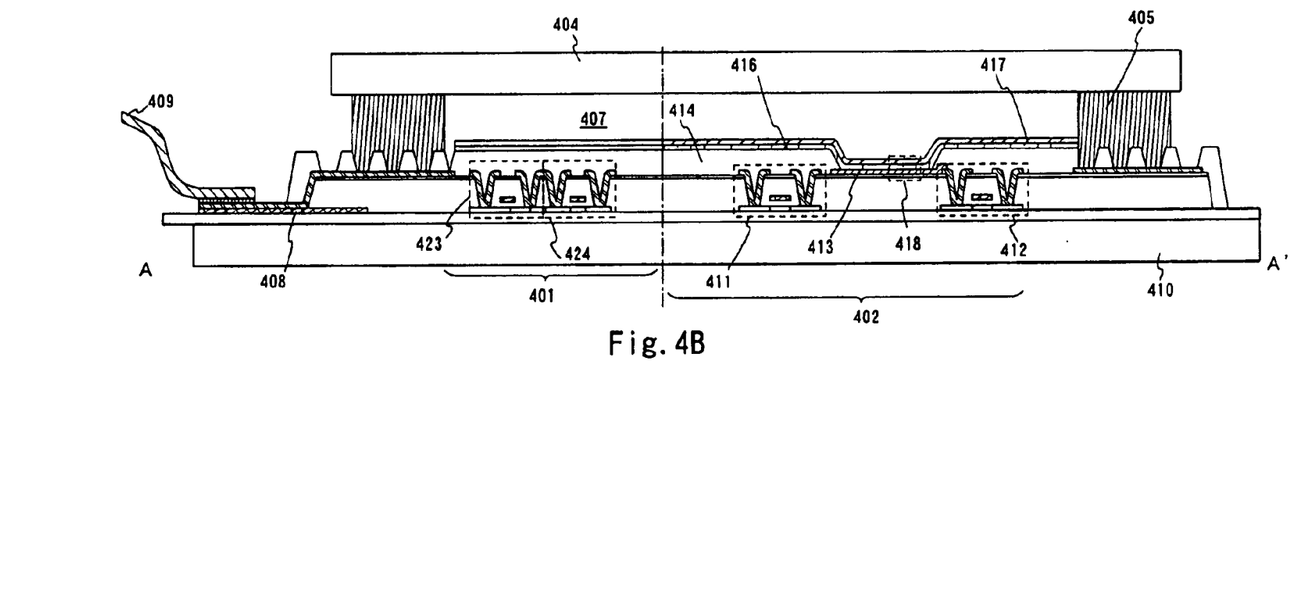

Hereinafter, a light-emitting device having a pixel portion composed of light-emitting elements according to the invention will be explained with reference to FIGS. 4A and 4B. FIG. 4A is a top surface view of the light emitting device. FIG. 4B is a cross-sectional view of FIG. 4A taken along the line A–A'. Reference numeral 401 shown by a dotted line denotes a driver circuit portion (a source driver circuit); 402, a pixel portion; and 403, a driver circuit portion (a gate side driver circuit). Furhter, reference numeral 404 denotes a sealing substrate; 405, sealing agent; and 407, space surrounded by the sealing agent 405.

Further, reference numeral 408 is a wiring for receiving video signals or clock signals from an FPC (Flexible Print Circuit) 409 serving as an external input terminal to transmit the received signals to the source signal line driver circuit 401 and the gate signal line driver circuit 403. Though only FPC is illustrated here, the FPC can be provided with a print wiring board (PWB). The light-emitting device accoridng to this embodiment includes a light-emitting device provided with an FPC or a PWB.

The cross-sectional structure is described with reference to FIG. 4B. A driver citcuit portoin and a pixel portion are formed over a substrate 410. Here, a source driver circuit 401 as a driver circuit portion and a pixel portion 402 are illustrated.

In the source driver ciruict 401, a CMOS ciruict is formed by an n-channel TFT 423 and a p-channel TFT 424. The TFT for forming a driver circuit may be formed by a known CMOS circuit, PMOS circuit, or NMOS circuit. In this embodiment, a driver integrated type in which a driver circuit is formed over a substrate is illustrated. However, the driver circuit can also be formed outside instead of over a substrate.

The pixel portion 402 is formed by a plurality of pixels including a switching TFT 411, a current control TFT 412, and a first electrode (anode) 413 connected electrically to the drain of the current control TFT 412. Further, an insulator 414 is formed to cover the edge portion of the first electrode 413. Here, the insulator 414 is formed by a positive type photosensitive acrylic resin film.

For improving the coverage, the upper edge portion or the lower edge portion of the insulator 414 is formed to have a curved surface having a radius of curvature. For example, when a positive photosensitive acrylic resin film is used for forming the insulator 414, it is preferable that only the upper edge portion of the insulator 414 is formed to have a curved surface having a radius of curvature (0.2 to 3 $\mu$m). As materials for the insulator 414, either a negative type photosensitive resin that becomes insoluble to etchant by light or a positive type photosensitive resin that becomes dissoluble to etchant by light can be used.

A layer containing light-emitting substances 416 and a second electrode 417 are formed over the first electrode 413, respectively. As a material for the first electrode 413 serving as an anode, a material having a large work function is preferably used. For instance, the first electrode can be formed by a single layer such as an ITO (indium tin oxide) film, an IZO (indium zinc oxide) film, a titanium nitride film, a chromic film, a tungsten film, a Zn film, or a Pt film; a lamination layer comprising one of the above single layer and a film containing mainly titanium nitride and aluminum; a three lamination layer comprising a titanium nitride film, a film containing aluminum as its main components, and another titanium nitride film; or the like. In case of adopting the lamination layer, the first electrode can be formed to have low resistance as a wiring, make good ohmic contact, and serve as an anode.

The layer containing light-emitting substances 416 is formed by vapor deposition using an evaporation mask, or ink jetting. The layer containing light-emitting substance 416 partly contains the organometallic complex according to the invention. Besides, as materials for forming the layer containing light-emitting substances 416, either a low molecular weight material or a high molecular weight material can be used. The layer containing light-emitting substance 416 is generally formed by a single layer or a lamination layer, each of which is formed by an organic compound; however, the layer containing light-emitting substance 416 according to this embodiment can be formed to contain a partly inorganic compound.

As a material for the second electrode (cathode) 417 formed over the layer containing light-emitting substance 416, materials having a small work function (Al, Ag, Li, Ca, or alloys of these elements such as MgAg, MgIn, Al—Li, $CaF_2$, or CaN) can be used. In case that light generated in the layer containing light-emitting substance 416 pass through the second electrode (cathode) 417, the second electrode (cathode) 417 is preferably formed by a lamination layer comprising a thin metal film and a transparent conductive film (alloys such as indium tin oxide (ITO), indium zinc oxide ($In_2O_3$—ZnO), zinc oxide (ZnO), or the like).

The sealing substrate 404 is pasted onto the substrate 410 with the sealing agent 405 to encapsulate a light-emitting element 418 within the space 407 surrounded by the substrate 410, the sealing substrate 404, and the sealing agent 405. The invention comprehends not only the case that the space 407 is filled with an inert gas (such as nitrogen or argon) but also the case that the space 407 is filled with the sealing agent 405.

The sealing agent 405 is preferably formed by epoxy-based resin. In addition, it is desirable that the material for the sealing agent inhibits the penetration of moisture or oxygen as much as possible. As materials for the sealing substrate 404, a plastic substrate such as FRP (fiberglass-reinforced plastics), PVF (polyvinyl fluoride), Myler, polyester, or acrylic can be used besides a glass substrate or a quartz substrate.

Accordingly, a light-emitting device comprising the light-emitting element according to the invention can be completed.

Example 2

Hereinafter, electronic equipment which is an application of the present invention will be explained. By applying the invention, the display function of electronic equipment mentioned below can operate at low voltage, that is, the power consumption can be reduced. By synthesizing the organometallic complex according to the invention with good yields, the cost of raw material for the electronic equipment can be reduced. Consequently, low-priced electronic equipment can be provided.

Figure 5A:
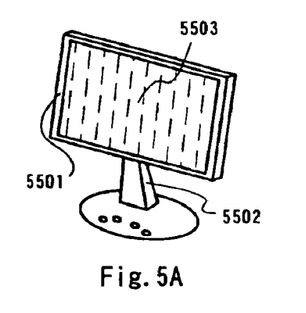
FIGS. 5A to 5F are explanatory views of electronic equipment applied with the invention.

FIG. 5A shows a display device composed of a frame 5501; a support 5502; and a display portion 5503. The invention can be applied to the display device having the display portion 5503.

Figure 5B:
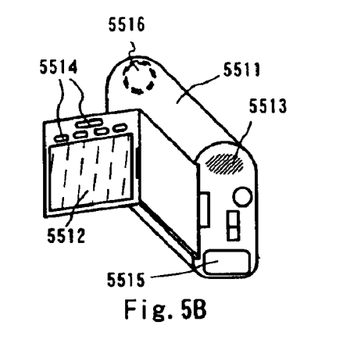

FIG. 5B shows a video camera composed of a main body 5511; a display portion 5512; a voice input portion 5513; operation switches 5514; a battery 5515; an image reception area 5516; and the like.

Figure 5C:
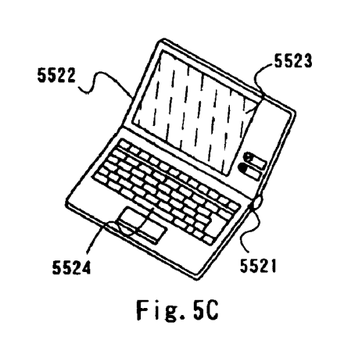

FIG. 5C shows a laptop computer manufactured according to the invention composed of a main body 5521; a frame 5522; a display portion 5523; a keyboard 5524; and the like.

Figure 5D:
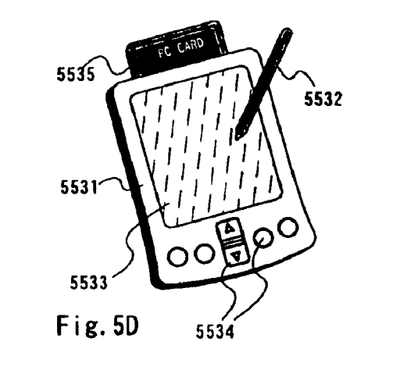

FIG. 5D shows a personal digital assistant (PDA) manufactured according to the invention composed of a main body 5531; a display portion 5533; an external interface 5535; operation switches 5534; and the like. The PDA also has a stylus 5532 as an attachment for the machine.

Figure 5E:
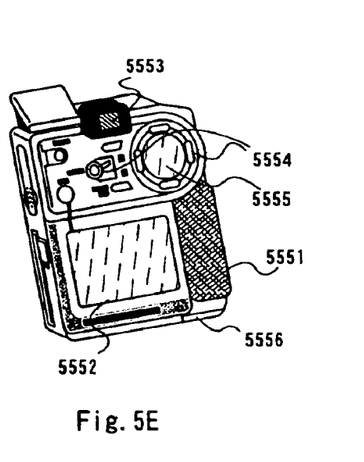

FIG. 5E shows a digital camera composed of a main body 5551; a display portion (A) 5552; an eye piece portion 5553;

operation switches 5554; a display portion (B) 5555; a battery 5556; and the like.

Figure 5F:
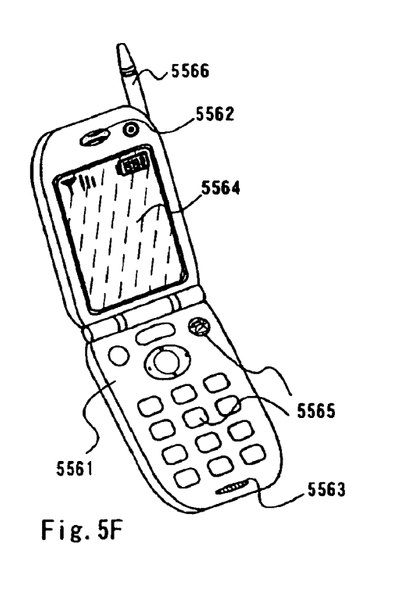

FIG. 5E shows a cellular phone manufactured according to the invention composed of a main body 5561; a display portion 5564; a voice output portion 5562; a voice input portion 5563; operation switches 5565; an antenna 5566; and the like.

According to the invention, organometallic complexes which can be formed with good yields and at low cost can be obtained. Further, organometallic complexes having excellent heat resistance properties can be obtained. Moreover, a light-emitting element can be formed to have excellent luminous efficiency by the organometallic complexes according to the invention.

Although the present invention has been fully described by way of examples with reference to the accompanying drawings, it is to be understood that various changes and modifications will be apparent to those skilled in the art. Therefore, unless otherwise such changes and modifications depart from the scope of the present invention hereinafter described, they should be construed as being included therein.

What is claimed is:

1. An organometallic complex represented by general formula 1, wherein each of $R^1$ to $R^5$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, wherein Y is a heterocyclic group containing a nitrogen atom as a hetero atom, wherein M is at least one of atoms of group 9 and group 10 in the periodic table, wherein when the M is the atom of group 9 in the periodic table, n=2, wherein when the M is the atom of group 10 in the periodic table, n=1, and wherein L is selected from the group consisting of a monoanionic bidentate chelate ligand having a beta diketone structure, a monoanionic bidentate chelate ligand having a carboxyl group and a monoanionic bidentate chelate ligand having a phenol hydroxyl group.

2. An organometallic complex according to claim 1, wherein each pair of R1 and R2, R2 and R3, and R4 and R5 is bonded each other to form aromatic rings.

3. An organometallic complex according to claim 1, wherein the Y is a heterocyclic group containing at least one of a five-membered ring and a six-membered ring.

4. An organometallic complex according to claim 1, wherein the M is at least one of an iridium atom and a platinum atom.

5. A phosphorescent material comprising the organometallic complex according to claim 1.

6. A light-emitting element having a layer comprising the organometallic complex according to claim 1 between a pair of electrodes.

7. An organometallic complex according to claim 1, wherein the L is represented by at least one of structural formulae 5 to 11.

8. An organometallic complex represented by general formula 2, wherein $R^{10}$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, wherein Y is a heterocyclic group containing a nitrogen atom as a hetero atom, wherein M is at least one of atoms of group 9 and group 10 in the periodic table, wherein when the M is the atoms of group 9 in the periodic table, n=2, wherein when the M is the atom of group 10 in the periodic table, n=1, and wherein L is selected from the group consisting of a monoanionic bidentate chelate ligand having a beta diketone structure, a monoanionic bidentate chelate ligand having a carboxyl group, and a monoanionic bidentate chelate ligand having a phenol hydroxyl group.

9. An organometallic complex according to claim 8, wherein the Y is a heterocyclic group containing at least one of a five-membered ring and a six-membered ring.

10. An organometallic complex according to claim 8, wherein the M is at least one of an iridium atom and a platinum atom.

11. A phosphorescent material comprising the organometallic complex according to claim 8.

12. A light-emitting element having a layer comprising the organometallic complex according to claim 8 between a pair of electrodes.

13. An organometallic complex according to claim 8, wherein the L is represented by at least one of structural formulae 5 to 11.

(5)

(6)

(7)

(8)

(9)

(10)

(11)

14. An organometallic complex represented by general formula 3, (3)

wherein each of $R^1$ to $R^9$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, wherein M is at least one of atoms of group 9 and group 10 in the periodic table, wherein when the M is the atom of group 9 in the periodic table, n=2, wherein when the M is the atom of group 10 in the periodic table, n=1, and wherein L is selected from the group consisting of a monoanionic bidentate chelate ligand having a beta diketone structure, a monoanionic bidentate chelate ligand having a carboxyl group, and a monoanionic bidentate chelate ligand having a phenol hydroxyl group.

15. An organometallic complex according to claim 14, wherein each pair of R1 and R2, R2 and R3, and R4 and R5 is bonded each other to form aromatic rings.

16. An organometallic complex according to claim 14, wherein the Y is a heterocyclic group containing at least one of a five-membered ring and a six-membered ring.

17. An organometallic complex according to claim 14, wherein the M is at least one of an iridium atom and a platinum atom.

18. A phosphorescent material comprising the organometallic complex according to claim 14.

19. A light-emitting element having a layer comprising the organometallic complex according to claim 14 between a pair of electrodes.

20. An organometallic complex according to claim 14, wherein the L is represented by at least one of structural formulae 5 to 11.

21. An organometallic complexes represented by general formula 4, wherein each of $R^6$ to $R^{10}$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, wherein M is at least one of atoms of group 9 and group 10 in the periodic table, wherein when the M is the atom of group 9 in the periodic table, n=2, wherein when the M is the atom of group 10 in the periodic table, n=1, and wherein L is selected from the group consisting of a monoanionic bidentate chelate ligand having a beta diketone structure, a monoanionic bidentate chelate ligand having a carboxyl group, and a monoanionic bidentate chelate ligand having a phenol hydroxyl group.

22. An organometallic complex according to claim 21, wherein each pair of R6 and R7, R7 and R8, and R8 and R9 is bonded each other to form aromatic rings.

23. An organometallic complex according to claim 21, wherein the Y is a heterocyclic group containing at least one of a five-membered ring and a six-membered ring.

24. An organometallic complex according to claim 21, wherein the M is at least one of an iridium atom and a platinum atom.

25. A phosphorescent material comprising the organometallic complex according to claim 21.

26. A light-emitting element having a layer comprising the organometallic complex according to claim 21 between a pair of electrodes.

27. An organometallic complex according to claim 21, wherein the L is represented by at least one of structural formulae 5 to 11.

28. An organometallic complex represented by general formula 24, (24)

wherein each of $R^1$ to $R^5$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, wherein Y is a heterocyclic group containing a nitrogen atom as a hetero atom, wherein M is at least one of atoms of group 9 and group 10 in the periodic table, wherein when the M is the atom of group 9 in the periodic table, n=2, and wherein when the M is the atom of group 10 in the periodic table, n=1.

29. An organometallic complex according to claim 28, wherein each pair of R1 and R2, R2 and R3, and R4 and R5 is bonded each other to form aromatic rings.

30. An organometallic complex according to claim 28, wherein the Y is a heterocyclic group containing at least one of a five-membered ring and a six-membered ring.

31. An organometallic complex according to claim 28, wherein the M is at least one of an iridium atom or a platinum atom.

32. A phosphorescent material comprising the organometallic complex according to claim 28.

33. A light-emitting element having a layer comprising the organometallic complex according to claim 28 between a pair of electrodes.

34. An organometallic complex represented by general formula 25, (25)

wherein $R^{10}$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, wherein Y is a heterocyclic group containing a nitrogen atom as a hetero atom, wherein M is at least one of atoms of group 9 and group 10 in the periodic table, wherein when the M is atom of group 9 in the periodic table, n=2, and wherein when the M is atom of group 10 in the periodic table, n=1.

35. An organometallic complex according to claim 34, wherein the Y is a heterocyclic group containing at least one of a five-membered ring and a six-membered ring.

36. An organometallic complex according to claim 34, wherein the M is at least one of an iridium atom and a platinum atom.

37. A phosphorescent material comprising the organometallic complex according to claim 34.

38. A light-emitting element having a layer comprising the organometallic complex according to claim 34 between a pair of electrodes.

39. A method for forming an organometallic complex comprising the step of:

forming a coordinate bond between a metal and a compound which is represented by general formula 12, (12)

wherein each of $R^1$ to $R^5$ is selected from the group consisting of a hydrogen atom, a halogen atom, a lower alkyl group, an alkoxy group, an acyl group, a nitro group, a cyano group, an amino group, a dialkylamino group, a diarylamino group, a vinyl group, an aryl group, and a heterocyclic group, and wherein Y is a heterocyclic group containing a nitrogen atom as a hetero atom.

40. A method according to claim 39, wherein each pair of $R^1$ and $R^2$, $R^2$ and $R^3$, and $R^4$ and $R^5$ is bonded each other to form aromatic rings.

* * * * *